United States Patent
Odermatt et al.

(10) Patent No.: US 9,370,604 B2
(45) Date of Patent: Jun. 21, 2016

(54) PLANAR IMPLANT

(75) Inventors: Erich Odermatt, Schaffhausen (CH);
Juergen Wegmann, Stockach (DE);
Bernd Blender, Hohentengen (DE)

(73) Assignee: Aesculap AG (DE)

( * ) Notice: Subject to any disclaimer, the term of this patent is extended or adjusted under 35 U.S.C. 154(b) by 1095 days.

(21) Appl. No.: 12/177,996

(22) Filed: Jul. 23, 2008

(65) Prior Publication Data
US 2009/0054995 A1 Feb. 26, 2009

(30) Foreign Application Priority Data

Jul. 24, 2007 (DE) .......... 10 2007 037 051

(51) Int. Cl.
| | | |
|---|---|---|
| *A61F 2/02* | (2006.01) | |
| *A61L 27/24* | (2006.01) | |
| *A61F 13/00* | (2006.01) | |
| *A61L 27/36* | (2006.01) | |
| *A61L 27/56* | (2006.01) | |
| *A61L 26/00* | (2006.01) | |

(52) U.S. Cl.
CPC . *A61L 27/24* (2013.01); *A61F 2/02* (2013.01); *A61F 13/00* (2013.01); *A61F 13/00029* (2013.01); *A61L 27/3604* (2013.01); *A61L 27/3675* (2013.01); *A61L 27/56* (2013.01); *A61L 26/0033* (2013.01); *A61L 26/0038* (2013.01)

(58) Field of Classification Search
CPC ..... A61L 27/24; A61L 27/3675; A61L 27/56; A61L 27/3604; A61L 15/00; A61L 26/0038; A61L 26/0033; A61L 27/222; A61L 27/3633; A61F 2/02; A61F 13/00; A61F 13/00012; A61F 13/00029; A61F 13/00008

USPC ........ 623/15.12, 23.71–23.76, 915, 918, 925; 606/213
See application file for complete search history.

(56) References Cited

U.S. PATENT DOCUMENTS

| | | | | |
|---|---|---|---|---|
| 4,759,354 | A * | 7/1988 | Quarfoot | 602/50 |
| 5,399,361 | A * | 3/1995 | Song et al. | 424/486 |
| 5,660,857 | A * | 8/1997 | Haynes et al. | 424/450 |
| 5,686,090 | A * | 11/1997 | Schilder et al. | 424/423 |
| 6,500,464 | B2 * | 12/2002 | Ceres et al. | 424/543 |
| 6,649,162 | B1 * | 11/2003 | Biering et al. | 424/94.64 |
| 6,942,961 | B1 * | 9/2005 | Baumgartner | 435/1.1 |
| 2002/0013627 | A1 | 1/2002 | Geistlich et al. | |
| 2003/0130747 | A1 * | 7/2003 | Abraham et al. | 623/23.72 |

(Continued)

FOREIGN PATENT DOCUMENTS

| | | |
|---|---|---|
| DE | 101 96 234 | 4/2003 |
| DE | 10 2005 054 940 | 5/2007 |

(Continued)

OTHER PUBLICATIONS

Dueck et al, "Experiment Investigation and Mathematical Modeling of the Thermal Shrinkage of Bovine Pericardium," Aug. 20, 2010, Journal of Medical and Biological Engineering, 31(3): 193-200.*

(Continued)

*Primary Examiner* — Jung Ou
(74) *Attorney, Agent, or Firm* — DLA Piper LLP (US)

(57) ABSTRACT

A planar implant for replacement of biological tissues includes a layered structure including
a) a lyophilized pericardium layer of biological origin, and
b) at least one sponge-like layer of lyophilized extracellular protein.

15 Claims, 1 Drawing Sheet

(56) References Cited

U.S. PATENT DOCUMENTS

| | | | |
|---|---|---|---|
| 2003/0133967 A1* | 7/2003 | Ruszczak et al. | 424/443 |
| 2003/0187515 A1* | 10/2003 | Hariri et al. | 623/23.72 |
| 2004/0059356 A1* | 3/2004 | Gingras | 606/151 |
| 2004/0078077 A1* | 4/2004 | Binette et al. | 623/13.17 |
| 2004/0107006 A1* | 6/2004 | Francis et al. | 623/23.72 |
| 2005/0232979 A1* | 10/2005 | Shoshan | 424/445 |
| 2007/0073415 A1 | 3/2007 | Sommerich | |
| 2007/0254016 A1* | 11/2007 | Andersen et al. | 424/443 |
| 2008/0033461 A1* | 2/2008 | Koeckerling et al. | 606/151 |
| 2008/0109017 A1* | 5/2008 | Herweck et al. | 606/151 |
| 2008/0181950 A1* | 7/2008 | Bates et al. | 424/484 |
| 2008/0195230 A1* | 8/2008 | Quijano et al. | 623/23.72 |
| 2008/0260801 A1* | 10/2008 | Ahlers et al. | 424/426 |

FOREIGN PATENT DOCUMENTS

| | | |
|---|---|---|
| EP | 1 738 780 A2 | 1/2007 |
| WO | 99/13902 A | 3/1999 |
| WO | 99/19005 | 4/1999 |
| WO | 01/19423 | 3/2001 |
| WO | 2006/045330 | 5/2006 |

OTHER PUBLICATIONS

Baharuddin, A. et al., "Bovine Pericardium for Dural Graft: Clinical Results in 22 Patients," *Clinical Neurology and Neurosurgery*, Netherlands, Sep. 2002, vol. 104, No. 4, pp. 342-344 (abstract only).

B. Braun Melsungen AG, "Lyoplant®," Apr. 15, 2008, along with an English translation.

* cited by examiner

PLANAR IMPLANT

RELATED APPLICATION

This application claims priority of German Patent Application No. 102007037051.4, filed Jul. 24, 2007, herein incorporated by reference.

TECHNICAL FIELD

This disclosure relates to a planar implant with a layered structure, the implant being suitable in particular for replacement of biological tissues.

BACKGROUND

The meninges are understood as the layers of connective tissue surrounding the brain and merging into the spinal meninx, which surrounds the rest of the central nervous system (CNS). The so-called dura mater is the outermost meningeal layer. It is composed of a largely taut and collagenous connective tissue and its main function is that of an organ capsule, in which role it prevents in particular an escape of the cerebrospinal fluid.

The dura mater is divided into two leaves, the outer leaf being identical to the periosteum in the region of the cranium. As a result, the dura mater, and in particular the underlying connective tissue, may possibly be damaged in neurosurgical operations, for example. The damage to the dura mater (outermost meningeal layer) may in these cases be so severe that replacement of at least parts of the dura mater may be necessary. Since the dura mater also has a very rich supply of blood vessels, such damage is often accompanied by severe bleeding.

It could therefore be helpful to make available an implant which can be used in particular for replacement of the dura mater and which has in particular good hemostatic and tissue-adhering properties.

SUMMARY

We provide a planar implant, in particular for replacement of biological tissues, with a layered structure composed preferably of:
  a) a lyophilized pericardium layer of biological origin, and
  b) at least one sponge-like layer of lyophilized extracellular protein.

We also provide a method for producing an implant including lyophilizing and connecting a pericardium layer and at least one layer of extracellular protein to each other.

We further provide a method of treating tissue defects including stopping or sealing leaking of liquid and/or air in a portion of a patient with the implant.

BRIEF DESCRIPTION OF THE DRAWINGS

Further details and features of our implants will become evident from the following description of preferred embodiments in the form of figures, examples and dependent claims. In these embodiments, individual features can be embodied singly or in combination with other features. All the figures are hereby expressly incorporated by reference into the content of this description.

In the attached figures.

DETAILED DESCRIPTION

Figure 1:
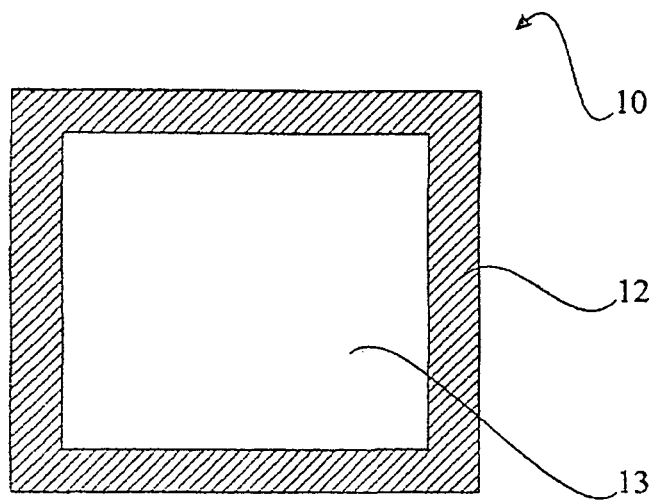
FIG. 1 shows a schematic plan view of an implant with protruding edges of the pericardium layer.

An implant is made available which, by virtue of its composite structure, has the advantageous properties both of a pericardium and also of a protein sponge. In accordance with the natural characteristics of a pericardium, the pericardium layer of the implant generally has a leather-like and therefore mechanically stable nature. The pericardium layer preferably serves as a kind of stabilizing substrate or support material for the sponge-like layer. In addition, the pericardium layer has the advantage that it has no real adhesive properties and therefore does not cause tissue adherences, for example to the cranial bone. The sponge-like protein layer preferably does have tissue-adherence properties. As a result, the implant can be placed directly onto the tissue to be treated, without the need for additional fixing steps, for example suturing. In other words, the implant advantageously has self-adherence properties. The adherence of the implant to tissue surfaces is attributable in particular to the capillary forces of the sponge-like protein layer. The moisture of the tissue serves here as adhesion promoter. The use of the implant can therefore also save the surgeon time. In addition, the robust and mechanically stable pericardium layer also allows the implant to be sutured, if necessary, to the treatment site or application site in the human or animal body. Thus, the implant can be sutured, for example, to hard tissue, in particular bone tissue. The implant can also advantageously take up liquids in a multiple of its own weight. The implant is therefore also suitable for the hemostatic treatment of wounds, since blood and, if appropriate, also exudate can be rapidly absorbed from the wound area through the sponge-like protein layer. At the same time, because of its normally leather-like consistency, the pericardium layer constitutes an impenetrable liquid barrier, such that the implant can also be used to achieve a tight closure of the application site in the human and/or animal body. This is of advantage particularly in sealing the dura mater, to avoid leakages of cerebrospinal fluid (CSF leakages).

The expression "sponge-like layer of lyophilized extracellular protein" signifies that the sponge-like layer is composed of one lyophilized extracellular protein or several lyophilized extracellular proteins and can contain, in addition to the extracellular protein or the extracellular proteins, further constituents, as will be described by way of example below.

The implant preferably has an at least two-layer structure. The implant can in particular be present in the form of a film.

In a preferred embodiment, the pericardium is xenogenic, in particular of bovine, procine or equine origin. The pericardium is usually a bovine pericardium.

Moreover, the extracellular protein can also be xenogenic, in particular of bovine, porcine or equine origin. Proteins of equine origin are particularly preferable because they pose particularly low risks of infection. The extracellular protein can also be a fibrous support protein. For example, the extracellular protein can be collagen and/or elastin. The extracellular protein is preferably collagen. The collagen can in particular be of type I, II, III and/or IV. The collagen is preferably of type I. The collagen can also be tendinous collagen.

In another embodiment, the extracellular protein is a plasma protein. Plasma proteins that can be used are in principle albumins and/or globulins and, in the case of globulins, these can especially be α1-globulins, α2-globulins and/or β-globulins. Moreover, the extracellular protein can also be a protein that inhibits blood coagulation, in particular macroglobulin and/or antithrombin. Another candidate is fibrinogen, the precursor of monomeric fibrin.

In a further embodiment, the extracellular protein is present in denatured form. For example, the extracellular protein can be present in the form of a partial hydrolysate. The extracellular protein is preferably gelatin. The gelatin preferably has a molecular weight (MW) of 100 to 500 kDa (kilodalton), in particular of 150 to 250 kDa. For example, the extracellular protein can be partially hydrolyzed gelatin with a molecular weight of up to 100 kDa. The gelatin can be characterized, for example, by a Bloom number of about 240. Gelatin also has the advantage of adhering particularly well to the tissue surface.

It is also possible for the extracellular protein to be of recombinant origin. For example, the extracellular protein can be produced by microorganisms, in particular yeast cells.

In a preferred embodiment, the extracellular protein is a mixture of different proteins, i.e., the sponge-like protein layer is a layer composed of several lyophilized extracellular proteins. For example, the protein mixture can be a mixture of gelatin and collagen. In this way, the good adherence properties of gelatin and the stable fiber properties of collagen can be combined particularly advantageously in the implant.

To increase the stability of the implant, the extracellular protein can in principle be crosslinked. The crosslinking can be a physical crosslinking or a chemical crosslinking. Possible crosslinking agents are preferably biocompatible molecules. The implant in this case preferably has a proportion of crosslinking agents that does not, from the medical point of view, lead to any relevant tissue damage. The crosslinking agents are preferably multifunctional compounds, preferably bifunctional compounds. Crosslinking agents that can be used here are in particular diamines, carbodiimides, diisocyanates, dicarboxylic acids, dialdehydes and/or polyaldehydes. The polyaldehydes are preferably polysaccharides carrying aldehyde groups (polyaldehydic polysaccharides). The polyaldehydic polysaccharides can have a degree of oxidation of 10 to 50%, preferably of 10 to 30%, preferably about 25%. The degree of oxidation is here to be understood as the proportion of monosaccharide units carrying aldehyde groups and, if appropriate, carboxyl groups in the polyaldehydic polysaccharide. The use of polysaccharides carrying aldehyde groups and with a lower degree of oxidation is particularly advantageous because of their more rapid resorbability. The carbodiimide can be EDC (1-ethyl-3-(3-dimethylaminopropyl)carbodiimide hydrochloride), for example. NHS (N-hydroxy succinimide) is also suitable for the crosslinking of the extracellular protein.

In a particularly preferred embodiment, the extracellular protein is uncrosslinked. The sponge-like layer is preferably free of crosslinking agents. This has the advantage that the sponge-like layer, and therefore the implant as a whole, can be degraded or resorbed more rapidly.

In principle, both sides of the pericardium layer can be covered with the sponge-like layer. The pericardium layer is preferably covered on one side with the sponge-like layer. In this embodiment, the mechanical stability of the pericardium layer can particularly advantageously be combined with the tissue-adherence properties in particular of the sponge-like protein layer.

In another embodiment, to achieve a connection between pericardium layer and protein layer that is as firm as possible, the surface of the pericardium layer directed toward the sponge-like layer is roughened. The pericardium is preferably roughened after its lyophilization. The pericardium surface is preferably roughened before the protein sponge is lyophilized onto the pericardium. The roughening can be carried out mechanically, in particular with the aid of a brush or a needle board. In addition, other methods can be used for treatment, in particular methods for activation, of the pericardium surface. For example, the surface of the pericardium layer can be activated by plasma treatment.

According to another embodiment, the sponge-like layer is lyophilized as substrate onto the pericardium layer. For this purpose, the pericardium, which has preferably been separately lyophilized in advance, is usually placed in a shaping arrangement, for example, in a lyophilization dish, covered with a dispersion of the extracellular protein and then lyophilized. The protein dispersion is preferably present as an aqueous dispersion to which, if appropriate, an alcohol can be added, for example, isopropanol, to increase the protein solubility. Alternatively, a moist or incompletely dried pericardium layer can be placed in a shaping arrangement, for example, a lyophilization dish, and covered or coated with a sponge-like layer of a previously lyophilized extracellular protein. A subsequent lyophilization leads to an implant.

In an alternative embodiment, the sponge-like layer is chemically fixed to the pericardium layer as substrate. The chemical fixing can be achieved by suitable crosslinking agents, for example. Regarding the properties and features of the possible crosslinking agents, reference is made to the above description.

The implant preferably has a thickness of 1 to 10 mm, in particular of 2 to 5 mm. The pericardium layer has in particular a thickness of 0.1 to 4 mm, preferably of 0.5 to 2 mm. The sponge-like layer of the extracellular protein preferably has a layer thickness of 1 to 10 mm, in particular of 2 to 5 mm, preferably of 3 to 4 mm.

In another embodiment, the implant has a weight per unit area of 80 to 480 g/m$^2$, in particular of 160 to 330 g/m$^2$. The weight per unit area of the pericardium layer is preferably between 50 and 180 g/m$^2$, in particular between 80 and 110 g/m$^2$. The sponge-like layer preferably has a weight per unit area of 30 to 300 g/m$^2$, in particular of 80 to 120 g/m$^2$. The density of the implant is preferably between 30 and 160 g/dm$^3$, in particular between 50 and 110 g/dm$^3$.

In another embodiment, the implant has protruding edges. The pericardium layer or the sponge-like protein layer in the implant can have protruding edges. In this way, depending on the intended purpose of the implant, emphasis can be placed more on the properties of the pericardium layer, in particular its mechanical stability, or on the properties of the sponge-like protein layer, preferably its tissue adherence properties, in the implant.

The sponge-like protein layer is preferably formed across the whole pericardium surface.

In a possible embodiment, the sponge-like layer is formed only partially on the surface of the pericardium layer. Provision can be made, for example, for the protein layer to be located only at points or on the outer edge of the pericardium layer.

It is also preferred for the sponge-like layer to contain at least one water-soluble biocompatible organic acid. The acid content in the sponge-like protein layer is preferably between 1 and 10% by weight, in particular between 2 and 8% by weight. The organic acid is preferably a nonvolatile acid. The organic acid can in particular be a low-molecular-weight acid. The acid is preferably an aliphatic acid. For example, the acid can have a carbon chain of 1 to 6 carbon atoms, preferably 3 to 6 carbon atoms. The acid can also be a polyvalent acid, in particular a divalent acid. Furthermore, the acid can be a hydroxycarboxylic acid, in particular a polyvalent hydroxycarboxylic acid. For example, the acid can be a sugar acid.

The water-soluble, biocompatible organic acid of the sponge-like protein layer is preferably an acid from the group comprising citric acid, tartaric acid, ascorbic acid, malic acid, gluconic acid, mucic acid, glutaric acid and adipic acid. Citric acid is particularly preferred.

The addition of acid to the sponge-like protein layer advantageously improves the liquid absorption capacity of the latter, in particular for body fluids, preferably for blood. In this way, the liquid absorption capacity of the implant as a whole can be increased. The sponge-like layer preferably has a liquid absorption capacity corresponding to 20 to 60 times, in particular 30 to 60 times its own weight. In this embodiment, the implant is particularly suitable for hemostasis.

In another embodiment, the sponge-like lay can be completely wetted with water with a period of <100 seconds, in particularly of <60 seconds, i.e., on its outer and inner surface. With regard to blood, the implant can preferably be completely wetted within a period of <180 seconds.

According to another embodiment, the sponge-like layer has a pH value of <4 upon addition of water. Preferably, the sponge-like protein layer has a pH of between 3.0 and 3.5 in water.

The implant, in particular the sponge-like protein layer, contains active substances. The active substances can in particular have antimicrobial properties. For example, the active substances can be antibiotics. The antibiotics can be gentamicin and/or rifampicin. Other active substances that can be used are biocompatible metal compounds, in particular metal salts, preferably silver salts. For example, the implant can contain silver acetate. Furthermore, the active substances can also be metals in an elemental state, which are preferably present in the form of nanoparticles. Thus, the implant can, for example, contain silver nanoparticles.

The active substances can also be anti-inflammatory compounds, in particular allatoin, saponin, riboflavin, flavonoids, tocopherol, betasitosterol, soledum cineol, dexpanthenol and/or bromalain. Preferred flavonoids are nobiletin, rutin and/or hesperidin.

In another preferred embodiment, the implant has at least one colored layer. The sponge-like layer of extracellular protein is preferably colored with at least one dye. The dye can, for example, entail D&C dyes (drug and cosmetic dyes), riboflavin, retinol and/or methylene blue. The coloring of the implant can be carried out in particular for improved recognition of its layers, in particular for easier distinction of the sponge-like protein layer from the pericardium layer.

The implant is preferably present in sterilized form. The sterilization methods that can be used are in principle all methods known to persons skilled in the art, for example, gamma-sterilization, electron irradiation, ethylene oxide gas sterilization or plasma sterilization. The implant can additionally be provided in a packaged form.

We also provide a method for producing the implant, wherein a pericardium layer and at least one layer of extracellular protein are lyophilized and connected to each other.

In a preferred embodiment, the method comprises the following steps:
  a) applying a liquid dispersion, which comprises an extracellular protein and at least one dispersion agent, to a pericardium layer,
  b) cooling and solidifying the applied dispersion to form at least one solid layer comprising the extracellular protein and the at least one dispersion agent,
  c) removing the dispersion agent by lyophilization to connect the layers to each other.

The pericardium layer is preferably lyophilized before application of the dispersion. The pericardium layer can be roughened after its lyophilization. In this connection, reference is made to the above description.

The liquid dispersion can be present in the form of a solution or suspension. The dispersion agent used is preferably water, to which an alcohol, in particular isopropanol, is optionally added to increase the solubility of the extracellular protein.

To apply the liquid dispersion to the pericardium layer, the latter can be transferred into a shaping arrangement, for example, into a lyophilization dish, and covered with the liquid dispersion. Alternatively, the liquid dispersion can also be introduced first of all into a shaping arrangement. In this case, the pericardium layer is then placed onto the dispersion. In both cases, the liquid dispersion is then cooled and solidified, and the liquid dispersion agent is removed by lyophilization.

To produce the implant, a liquid dispersion is preferably used with a proportion of the extracellular protein of between 0.1 and 5% by weight, in particular of between 0.2 and 2.5% by weight, relative to the total weight of the liquid dispersion. If the extracellular protein is gelatin, then a dispersion is preferably used with a gelatin proportion of between 0.2 and 0.5% by weight relative to the total weight of the liquid dispersion. In the case where collagen is sued as the extracellular protein, a collagen dispersion is preferably used in which the proportion of collagen is between 2 and 2.5% by weight relative to the total weight of the dispersion. The lyophilization is preferably carried out in a temperature range of between $-10°$ C. and $-50°$ C., in particular between $-20°$ C. and $-40°$ C.

In an alternative embodiment, a moistened or still not completely dried pericardium layer is covered or coated with an already lyophilized layer of the extracellular protein and is then subjected to a lyophilization to connect the two layers to each other. For further features and details, reference is made to the above description.

The implant is generally suitable in a particularly advantageously manner for the treatment, in particular the replacement and/or closure, of tissue defects, preferably soft-tissue defects. The implant is preferably used to stop or seal leaking of liquid or air in the human and/or animal body.

The implant is preferably used for the replacement and/or closure of the dura mater, in which case the implant is preferably configured as a dura mater onlay. The implant can be used in particular to seal a damaged dura mater, without dura mater tissue first of all being removed from the patient. The implant is suitable in particular for sealing off the cerebrospinal fluid of the brain. These sealing properties of the implant can be achieved in particular by means of its pericardium layer, which generally constitutes a kind of absolute physical barrier to liquids, in particular to body fluids. By contrast, in conventional pure protein sponges, there is a danger that if their maximum liquid absorption capacity is exceeded, further amounts of liquid will no longer be able to be held back. Moreover, if so desired, the implant can also be sutured to the dura mater via the pericardium layer.

By virtue of the tissue adherence properties of its sponge-like protein layer, the implant can also be used as a hemostatic agent or hemostyptic. In this form, the implant can be used to arrest the bleeding of internal wounds, in particular of parenchymal organs, for example, of the liver, spleen, pancreas, kidneys, lungs, adrendal glands, but also for treatment of the thyroid gland and/or lymph nodes. The implant is also suitable for thoracic interventions, for example, for closing or sealing air leaks in the lungs. It is also possible for the implant to be used in gastrointestinal operations, in particular for sealing anastomoses of the intestines. A further possible use of the implant is to cover urethral erosions. In the aforementioned applications, the mechanically stable, in particular tear-resistant nature of the pericardium layer means that the implant can be sutured particularly advantageously onto the respective wound. This is not possible when using an implant composed exclusively of collagen.

We further provide a surgical method for the treatment of tissue defects, in particular for the replacement and/or closure of biological tissues, wherein a planar implant with a layered structure preferably composed of:

a) a lyophilized pericardium layer of biological origin, and
b) at least one sponge-like layer of lyophilized extracellular protein, is implanted into the body of a patient to treat one of the indications described above. The surgical method is preferably used to stop or seal leaking of liquid and/or air in the body of a patient. For further details and features, reference is therefore made to the above description.

DETAILED DESCRIPTION

FIG. 1 shows a schematic plan view of an implant 10 with a two-layer structure composed of a lyophilized pericardium layer 12 and a sponge-like layer 13 with a lyophilized extracellular protein 13. The pericardium layer 12 has protruding edges in the implant 10. The larger surface of the pericardium layer 12 gives the implant 10 particularly stable properties. For example, the protruding edges of the pericardium layer 12 can be used for suturing the implant 10 onto a wound.

Figure 2:
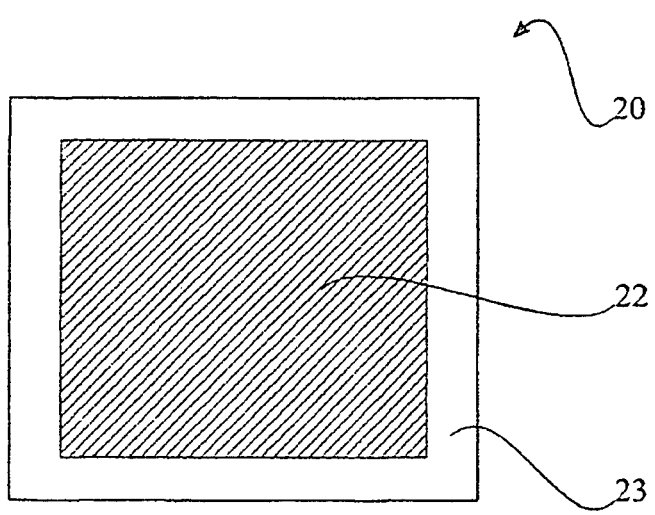
FIG. 2 shows a schematic plan view of an implant with protruding edges of the sponge-like protein layer.

FIG. 2 shows a schematic plan view of an implant 20 with a two-layer structure composed of a lyophilized pericardium layer 22 and a sponge-like layer 23 with a lyophilized extracellular protein. The sponge-like protein layer 23 has protruding edges in the implant 20. In this way, the tissue adhesion properties of the implant 20 can be improved in particular.

Figure 3:
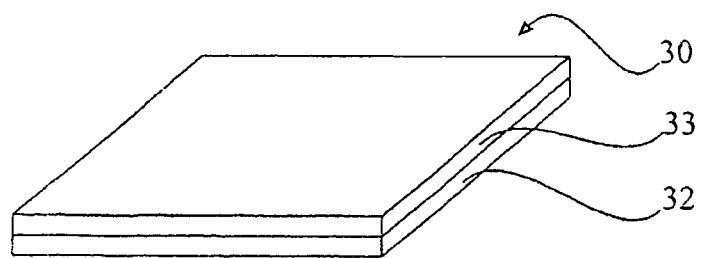
FIG. 3 shows a schematic view of an implant.

FIG. 3 is a schematic view of an implant 30 with a two-layer structure composed of a lyophilized pericardium layer 32 and a sponge-like layer 33 of lyophilized extracellular protein.

Example 1

Production of Implants a) Freeze-dried bovine pericardium was cut to a size of 10×14 cm and roughened with a brush. Thereafter, 6.6 g of collagen were swollen in 132 ml of ultrapure water (milliQ water from Millipor, Germany) that contained additives of acetic acid. The swollen collagen was suspended for 20 minutes in a solvent mixture of 231 ml ultrapure water and 33 ml isopropanol. Thereafter, 264 mg of malic acid (0.1% by weight relative to the total weight of the suspension) were dissolved in 264 ml of the suspension. Thereafter, 65 g of the suspension were poured in each case onto lyophilization dishes with a base surface area of 165 cm$^2$. The cut sections of bovine pericardium were placed with the roughened surface onto the suspension. The composition was then freeze-dried at −40° C. and lyophilized. Rectangular plates of bovine pericardium coated with a collagen sponge were obtained as products, in which the sponge was applied in a mechanically firm manner on the bovine pericardium and this composite structure remained stable in particular when immersed in water.

b) 2.64 g of acetic acid and 6.6 g of collagen were weighed into 132 ml of ultrapure water (MilliQ from Millipore, Germany). The collagen was left to swell for a total of 16 hours. Thereafter, the swollen collagen was washed several times with ultrapure water and suspended for 20 minutes in a mixture of 231 ml ultrapure water and 33 ml isopropanol. Thereafter, 65 g of the suspension were poured in each case into a lyophilization dish with a base surface area of 165 cm$^2$. This was followed by lyophilization. The collagen plates obtained after lyophilization were removed from the dishes and stored dry until further processing. Processed and defatted sections of bovine pericardium were moistened with ultrapure water and placed in the lyophilization dishes described above. The collagen plates were then placed onto the pericardium. The dishes were then frozen and lyophilized. Rectangular sections of bovine pericardium coated with a collagen sponge were obtained as precuts, in which the sponge was applied firmly on the bovine pericardium. The composite structure of the implant remained stable when immersed in water.

In a parallel test, pure collagen sponges, i.e., without pericardium, were produced by lyophilization.

Example 2

Behavior with Respect to Heparinized Blood

The implants produced in Example 1 were cut into sections measuring 3×5 cm. 150 ml of fresh heparinized pig's blood were placed in a crystallization dish. An implant and a pure collagen sponge were placed at the same time on the surface of the blood, the sponge-like protein layer being applied directly on the blood surface. The time needed for complete penetration of blood through the implants was then measured. While the pure collagen sponge was completely saturated with blood after 50 seconds, it was observed that no blood at all had penetrated through the bovine pericardium even after 60 minutes. This observation corroborates the sealing action of the pericardium component of the implant with respect to body fluids, in particular blood.

The implant was then weighed. It was found that the implant had taken up 10 times its own weight of blood. Relative to the collagen sponge on its own (less the weight of the pericardium), the amount of blood taken up corresponded to 27 times the inherent weight of the collagen sponge applied to the pericardium. This illustrates the high degree of absorbency of the collagen sponge in the implant.

Example 3

In Vitro Tests 3.1 Determination of Punch-Through Force

Circular sections with a diameter of 45 mm were cut out from Lyoplant® (freeze-dried bovine pericardium from B/Braun Aesculap AG, Tuttlingen, Germany) and from composite implants produced according to Example 1. The sections were secured in a holder with a clamping diameter of 25 mm. To determine the punch-through force, a punch (diameter 12.5 mm) was pressed at a speed of 50 mm/min centrally through the clamped test pieces, and the forces required were detected. The results given in Table 3.1 show that essentially the same punch-through forces had to be applied in the Lyoplant® product and in the implants produced according to Example 1. This illustrates that the mechanical stability or strength of the pericardium in the implant is maintained.

TABLE 3.1

Comparison of average punch-through force

| | Punch-through force | Standard deviation |
|---|---|---|
| Implant according to Example 1 | 145N | 22N |
| Lyoplant ® | 164N | 31N |

3.2 Thread Tear-Out Force

Rectangular strips with a length of 30 mm and a width of 25 mm were cut out from Lyoplant® (freeze-dried bovine pericardium B/Braun Aesculap AG, Tuttlingen, Germany) and from the composite implants produced according to Example 1. Thereafter, a Safil® thread (B/Braun, Aesculap, Tuttlingen, Germany) of strength USP 2.0 was drawn through the implant 1 cm under the cut edge, and the implant was clamped in the lower clamping jaw of a tensile test machine (from Zwick Roell, Ulm, Germany). Thereafter, the thread was secured in the upper holder; the spacing of the clamping jaws was 7 cm. The thread tear-out force was measured at a pulling speed of 300 mm/min. The results reproduced, in Table 3.2 show that very similar thread tear-out forces were measured for the product Lyoplant® and for the implants produced according to Example 1b).

TABLE 3.2

Comparison of mean thread tear-out force

| | Thread tear-out force | Standard deviation |
|---|---|---|
| Implant according to Example 1 | 26.4N | 13.4 |
| Lyoplant ® | 27.3N | 12.5 |

In contrast to conventional self-adhesive collagen sponges, our implant has the advantage that it can be sutured. Suturing is especially advantageous in large defects of the dura mater, for example, of the kind that occur when the dura mater tissue is tumorous, since in these cases the endogenous dura mater is not completely available as a support surface for the implant, and the implant therefore has to be secured to the cranial bone with the aid of suture material.

3.3 Breaking Strength Measurements

Rectangular strips with a length of 100 mm and a width of 25 mm were cut out from Lyoplant® (freeze-dried bovine pericardium B/Braun Aesculap AG, Tuttlingen, Germany) and from the composite implants produced according to Example 1. The strips were clamped in the clamping jaws (spacing 7 mm) of a tensile test machine and pulled apart with a pull speed of 50 mm/min. The breaking strength was measured in each case on n=7 samples.

TABLE 3.3

Comparison of means break strength

| | Breaking strength | Standard deviation |
|---|---|---|
| Implant according to Example 1 | 211N | 75N |
| Lyoplant ® | 187N | 26N |

The results given in Table 3.3 show that the breaking strength of our implant is comparable to the breaking strength of Lyoplant®.

Overall, the tests described in Examples 3.1 to 3.3 show that the material-related properties of our implant in terms of punch-through force, thread tear-out force and breaking strength are comparable to pure bovine pericardium and are therefore not adversely altered by the layered structure of our implant. These properties make the implant particularly useful, for example, as a replacement material for the dura mater, in particular as a dura mater onlay.

3.4 Water Absorption Capacity

Rectangular strips with a length of 100 mm and a width of 25 mm were cut out from Lyoplant® (freeze-dried bovine pericardium B/Braun Aesculap AG, Tuttlingen, Germany) and from the composite implants produced according to Example 1. The strips were then placed in a Petri dish with 20 ml of water. After the implants were completely saturated with water, the water absorption capacity was measured using the following formula:

$$X = \frac{W_{wet} - W_{dry}}{W_{wet}} \cdot 100\%$$

TABLE 3.4

Comparison of mean water absorption capacity

| | Water absorption capacity | Standard deviation |
|---|---|---|
| Implant according to Example 1 | 1565% | 93% |
| Lyoplant ® | 542% | 106% |

It was found that our implant is stable in water. In particular, there was no sign of the layers coming loose from each other. In addition, neither the Lyoplant® product nor our implant swelled in water, which is advantageous in particular for use in neurosurgery, since implants that swell can generally lead to complications (pain, high cerebral pressure). A total of n=6 measurements were carried out.

Example 4

Animal Experiments

In an animal study including 6 pigs (animals 1, 2, 3, 4, 5 and 6), our implant was tested to compare it to pure bovine pericardium (without additional collagen sponge). After the animals had been anesthetized, an incision measuring approximately 6 cm in length was made above the ear, and the bleeding thus caused was arrested by conventional surgical methods. Thereafter, a surgical drill was used to perform a craniectomy with a diameter of 4 cm, to expose the dura mater of the animals. Thereafter, a defect with a diameter of 2.5 cm was formed in the dura mater. Lyophilized bovine pericardium (Lyoplant®, B/Braun Aesculap, Tuttlingen, Germany) was then cut to the size of the defects in animals 1, 3 and 5 and was secured with a running stitch to the remaining dura mater of these animals. The average time between the application of the bovine pericardium and the intraoperative testing of leaktightness to cerebrospinal fluid (CSF) was 18 minutes. In parallel, an implant produced according to Example 1 was cut to the defect size for animals 2, 4 and 6 and then placed onto the defects of these animals. The average time between the application of the implant and the intraoperative testing of CSF leaktightness was 5 minutes, which clearly demonstrates the advantage of the surgeon being saved time.

After application, the Valsalva maneuver was used to test the leaktightness of the implant, before the wound was closed (Table 4). The animals were dissected after 28 days. The animals were anesthetized again, and the wound area of the dura mater was exposed. The implants (Lyoplant® and our implants) could still be seen in all the animals. Before histological samples were removed, the leaktightness of the dura mater closure was again tested using the Valsalva maneuver (Table 4). The macroscopic findings and the histological findings showed that no adhesions between the meninges and the brain had occurred in any of the animals. Moreover, the wound healing and the incorporation of the implants into the dura mater were assessed as very good. The minimal inflammatory reactions that occurred were attributable to the natural healing of the wound.

TABLE 4

Induced intercranial pressure

| Implant | Animal No. | Intraoperative CSF leaktightness | CSF leaktightness at dissection |
| --- | --- | --- | --- |
| Implant according to Example 1 | 2 | 2.2 kPa | 2.2 kPa |
| Implant according to Example 1 | 4 | 2.2 kPa | 2.2 kPa |
| Implant according to Example 1 | 6 | 2.2 kPa | 2.2 kPa |
| Lyoplant ® | 1 | 2.2 kPa | 2.2 kPa |
| Lyoplant ® | 3 | 1.1 kPa | 2.2 kPa |
| Lyoplant ® | 5 | 2.2 kPa | 2.2 kPa |

The animal study shows that the functionality and safety of the pericardium layer in our implant is comparable to the functionality and safety of the product marketed by the assignee herein under the name Lyoplant®. A particular advantage over the commercially available product Lyoplant® is that the sealing action of our implant has a much quicker onset, resulting in a time saving for the surgeon. It is in this way possible to reduce the costs of surgical interventions, in particular neurosurgical interventions. This applies also to larger tissue defects, which can be treated with the implant.

Overall, the tests described in the examples confirm that, by virtue of its special material-related properties, our implant can be sutured to tissue and can also adhere to tissue. Our implant is therefore characterized in a particularly advantageous manner by the fact that, on the one hand, it is self-adhesive and, on the other hand, can still be sutured on, if this is desired in view of the specific nature of the tissue defect that is to be treated.

The invention claimed is:

1. A planar implant for replacement of biological tissues consisting of a layered structure consisting of:
   a) a lyophilized pericardium layer of biological origin, wherein the pericardium layer constitutes an impenetrable liquid barrier, and wherein the pericardium layer has a weight per unit area of 50 to 180 g/m², and
   b) at least one sponge layer of lyophilized extracellular protein which is free of crosslinking agents,
   wherein the implant has a thickness of 1 to 10 mm, a weight per unit area of 80 to 480 g/m² and the implant is configured to replace and/or close the dura mater.

2. The planar implant according to claim 1, wherein the extracellular protein is collagen.

3. The planar implant according to claim 1, wherein the extracellular protein is gelatin.

4. The planar implant according to claim 1, wherein the pericardium layer is covered on one side with the sponge layer.

5. The planar implant according to claim 1, wherein a surface of the pericardium layer directed toward the sponge layer is roughened.

6. The planar implant according to claim 1, wherein the sponge layer is lyophilized as substrate onto the pericardium layer.

7. The planar implant according to claim 1, wherein the sponge layer is fixed to the pericardium layer.

8. The planar implant according to claim 1, wherein the pericardium layer has a thickness of 0.1 to 4 mm.

9. The planar implant according to claim 1, wherein the sponge layer has a weight per unit area of 30 to 300 g/m².

10. The planar implant according to claim 1, wherein the sponge layer is formed only partially on the pericardium layer.

11. The planar implant according to claim 1, wherein the sponge layer has a pH value of <4 upon addition of water.

12. The planar implant according to claim 1, wherein the sponge layer has a liquid absorption capacity corresponding to 20 to 60 times its own weight.

13. The planar implant according to claim 1, wherein the sponge layer can be completely wetted with water within a period of <100 seconds.

14. A planar implant for replacement of biological tissues consisting of a layered structure consisting of:
   a) a lyophilized pericardium layer of bovine origin, wherein the pericardium layer constitutes an impenetrable liquid barrier and has a weight per unit area of 50 to 180 g/m², and
   b) at least one sponge layer of lyophilized collagen of bovine origin which is free of crosslinking agents, wherein the sponge layer has a weight per unit area of 30 to 300 g/m², a liquid absorption capacity corresponding to 20 to 60 times its own weight, and is configured to be wetted with water with a period of <100 seconds,
   wherein the implant has a thickness of 1 to 10 mm, a weight per unit area of 80 to 480 g/m² and is configured to replace and/or close the dura mater.

15. A planar implant for replacement of biological tissues consisting of a layered structure consisting of:
   a) a lyophilized pericardium layer of bovine origin, wherein the pericardium layer constitutes an impenetrable liquid barrier, and has a weight per unit area of 50 to 180 g/m²,
   b) at least one sponge layer of a lyophilized suspension of collagen of bovine origin which is free of cross-linking agents and contains at least one water-soluble biocompatible organic acid, wherein the sponge layer has a weight per unit area of 30 to 300 g/m², a liquid absorption capacity corresponding to 20 to 60 times its own weight, and is configured to be wetted with water with a period of <100 seconds,
   wherein the implant has a thickness of 1 to 10 mm, a weight per unit area of 80 to 480 g/m² and is configured to replace and/or close the dura mater.

* * * * *